(12) United States Patent
Maanum

(10) Patent No.: US 9,103,752 B1
(45) Date of Patent: Aug. 11, 2015

(54) METHOD AND APPARATUS FOR MANAGING RADON GAS

(71) Applicant: Armand D. Maanum, Golden Valley, MN (US)

(72) Inventor: Armand D. Maanum, Golden Valley, MN (US)

( * ) Notice: Subject to any disclaimer, the term of this patent is extended or adjusted under 35 U.S.C. 154(b) by 0 days.

(21) Appl. No.: 14/293,265

(22) Filed: Jun. 2, 2014

(51) Int. Cl.
   *G01N 1/12* (2006.01)
   *G01N 1/22* (2006.01)
   *G01N 1/14* (2006.01)

(52) U.S. Cl.
   CPC .............. *G01N 1/2247* (2013.01); *G01N 1/14* (2013.01)

(58) Field of Classification Search
   CPC ....................................................... G01N 1/14
   USPC ....................................................... 73/864.51
   See application file for complete search history.

(56) References Cited

U.S. PATENT DOCUMENTS

| | | | | |
|---|---|---|---|---|
| 4,820,925 A | * | 4/1989 | Balmer et al. | 250/379 |
| 4,963,730 A | * | 10/1990 | Tetley et al. | 250/253 |
| 5,403,383 A | * | 4/1995 | Jaisinghani | 95/69 |
| 5,451,929 A | * | 9/1995 | Adelman et al. | 340/521 |
| 6,184,531 B1 | * | 2/2001 | Smart et al. | 250/370.01 |
| 2003/0030444 A1 | * | 2/2003 | Kogawa et al. | 324/464 |
| 2011/0033346 A1 | * | 2/2011 | Bohlen et al. | 422/186.3 |

* cited by examiner

*Primary Examiner* — Hezron E Williams
*Assistant Examiner* — Rodney T Frank
(74) *Attorney, Agent, or Firm* — Merchant & Gould P.C.

(57) ABSTRACT

A radon collection cartridge and a radon extraction system for economically reducing or removing radon gas danger are disclosed. The cartridge and system can include one or more screens having a plurality of spaced openings. Loosely stacked screens can be secured within a frame to form a cartridge with a labyrinth-like airflow path. At least some of the screens are provided with a surface that collects and retains radon materials. The radon extraction system can include at least one of the above described screens or cartridges. The system may also include a fan assembly having a motor connected to a fan wheel to induce an air flow through the screen(s) or cartridge(s). A controller may be provided that operates the fan assembly motor. The controller can operate the fan motor based on the operational state of a gas burning appliance.

13 Claims, 12 Drawing Sheets

METHOD AND APPARATUS FOR MANAGING RADON GAS

BACKGROUND

Radon gas, for a great period of time, existed as a deadly unknown danger to all life. Since 1300 AD, in history accounts of Eastern Europe, the existence and effects of radon gas has confounded many thousands of scientists and observers for over the last seven hundred years. Radon gas was recognized as a named danger in the year 1900 AD by a noted research doctor-scientist, Dr. Frederich Dorn, who named it "R 222." The name was amended, upon further reviews to Radon gas 222, a dangerous lethal radioactive gas. Unknown or defined for hundreds of years, radon gas has been feared or accepted as "can't fix it or learn to live with it", the will of the Gods, or witchcraft for hundreds of years.

Researchers and scientists, worldwide, have studied and tried to eliminate this danger. There are literally countless studies and proposed answers that accomplish almost nothing to resolve the dangers of radon gas, because the gas continuously emanates and seeps to the entire surface of the planet, except where the formation of natural substances obstructs the seep of the gas and its subsequent half-life decay to its final reality (lead). It can't be stopped. An unnamed Berlin researcher was quoted as saying that 70% of man's ills/aging, relate to radon. Furthermore, according to the National Cancer Institute (see www.cancer.gov), radon is the second leading cause of lung cancer in the United States with scientists estimating that 15,000 to 22,000 lung cancer deaths in the United States each year are related to radon. Also, "Radon is likely our leading environmental cause of cancer mortality in the United States. During the past 50 years, over a million people have died nationwide from radon-related lung cancer." (Testimony from R. William Field, University of Iowa professor of occupational and environmental health and epidemiology to President's Cancer Panel in 2010.)

SUMMARY

The inventor of this application became interested in the radon gas problem after age 80 because, as a boy at age 10, in 1940, he had read a science journal listing scientific oddities and unknowns describing the element Uranium (U-235) as a possible explosive material and atomic bomb possibility. The inventor also read a second article of a mysterious well in the State of Texas that spouted helium gas. The mention of helium in an article in recent years regarding "Radon, Impossible Danger etc." caught the inventor's eye.

The inventor's device described herein has been tested in a closed and undisturbed space, such as a residential basement, as an improvement testing area for final product qualities. This device is to fix the problem of radon gas infiltration, which has been mistakenly ignored since the problem was until then, actually invisible, and thus not even tested for and therefore instruments to test for this were not available. The inventor's research made him realize a major error had been made in radon danger priority.

The disclosed invention is designed to significantly reduce radon related health problems. A six to seven inch high full directed air flow, treated cartridge, capable of fitting in specially designed accessories is disclosed. In one aspect, a low flow, constant slow running suction fan driven by an adjustable rate motor is provided to allow the airflow through the cartridge to mimic the same as the combustion gases up the chimney and the chimney effect suction when winds flow across it. The flow is slow enough so as to not disturb the "surface tension" of the "r gas" in that six to seven inch level (seepage and settled gas). This invention and system and its various accessories and applicators are designed to economically reduce or remove radon gas danger, thereby saving millions of lives, saving billions of expenses of the Affordable Care Act (ACA), creating new jobs, and serving as the basis of new legislation by US and health organizations, and especially the EPA of the USA. It is believed that savings to the ACA and to families will make the minor installations a zero net cost or net savings proposition.

In one aspect, the disclosure is directed to a radon collection cartridge having a plurality of stacked screens having a plurality of spaced openings. The stacked screens can be secured within a frame to form a cartridge. In one embodiment, at least some of the screens are provided with a surface having a negative charge. In one embodiment, all of the screens are provided with a surface having a negative charge. In one embodiment, the screens are provided with a surface or coating that serves as the negative charge to attract, collect, and retain radon and radon decay products, which may be attached or unattached to dust particles. In one embodiment, the coating is at least one of magnesium fluoride and magnesium oxide which can be relatively inexpensive materials that are easily obtained for use in manufacture. In one embodiment, the coating is a mixture of magnesium fluoride and magnesium oxide. In one embodiment, the coating is about one half, by weight, magnesium fluoride and one half, by weight, magnesium oxide.

In one aspect, the disclosure is directed to a radon extraction system including at least one radon collection device, which may include at least one screen having a plurality of spaced openings and a provided with a surface or coating to attract, collect, and retain radon and radon decay products which may be attached or unattached to dust particles. In one embodiment, the system includes one or more of the above described cartridges. The system may also include a fan assembly having a motor connected to a fan wheel that is constructed and arranged to induce a slow moving air flow through at least one screen when the motor is activated. Additionally, a controller may be provided that selectively activates and deactivates the fan assembly motor. In one embodiment, the controller activates and deactivates the fan assembly motor based on the operational state of a gas burning appliance.

In one aspect, a method for collecting radon materials is disclosed in which a radon collection device having a plurality of stacked screens is provided. An entering airflow stream containing radon materials is allowed or caused to flow into the radon material collection device and across the plurality of stacked screens. As the airflow stream passes through the device, at least some of the radon materials from the airflow stream are collected and retained on at least some of the stacked screens. Subsequently, the airflow stream is allowed or caused to flow out of the device at which time the exiting airflow stream includes less radon materials than the entering airflow stream.

The inventor of the subject matter disclosed herein believes the designating term "Radabater" may be used as a source indicating mark for products, components, and/or methods using the disclosed technology and arrangements.

DESCRIPTION OF THE DRAWINGS

Non-limiting and non-exhaustive embodiments are described with reference to the following figures, which are

DETAILED DESCRIPTION

Figure 1:
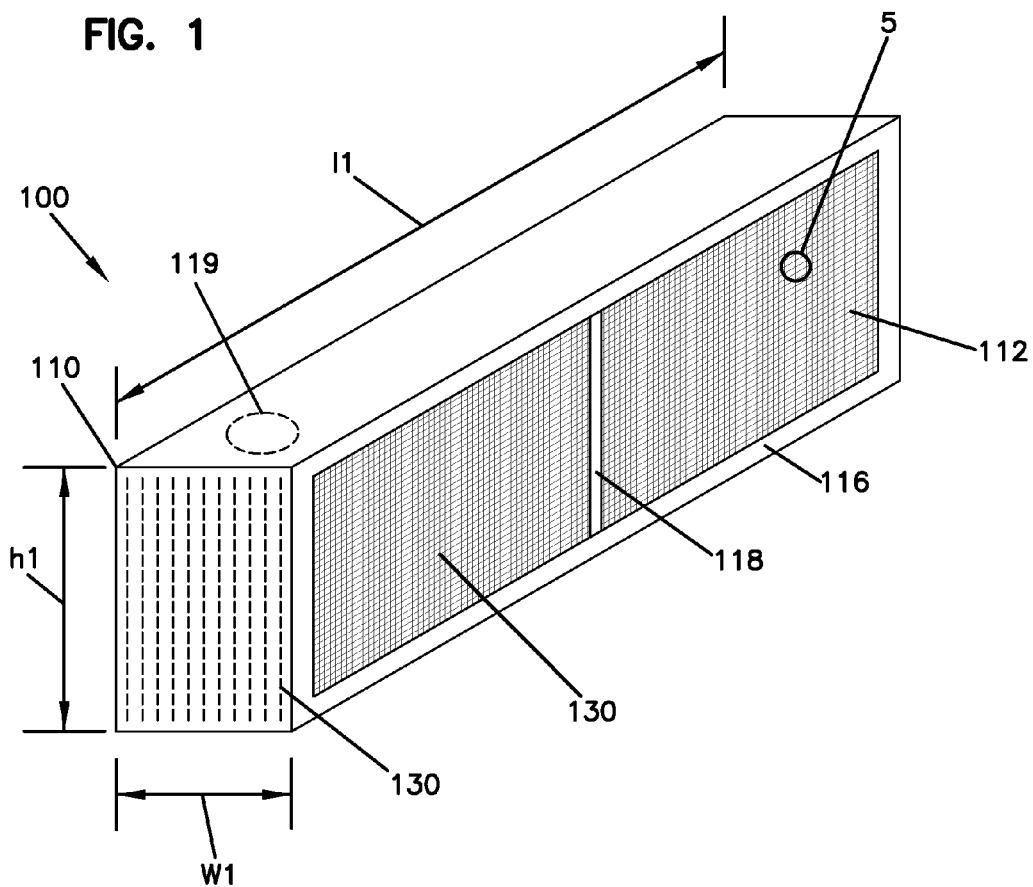
FIG. 1 is a perspective view of a cartridge having features that are examples of aspects in accordance with the principles of the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

A curie or micro-curie (Mc) is a measure of radiation by Pierre and Marie Curie (1903 Nobel prize Physics). An average measure (many languages-countries etc.) of tested radiation levels that accumulate in a closed undisturbed room (initially "cleaned to zero") is about 3.643 Mc. The inventor, performing his own calculations, realized with given figures for Radon 222 (a half life of 3.82 days and an end half life of 180.117 Mc), that it has become possible to prove seepage and decay products and balance the 180.117Mc, verified half-life period with continual seepage added, to result in within millionths of billionths of vibrations to be that of the average of 3.643Mc to be most correct.

Ideally, the seepage must be removed as immediately as possible, even as the decay is continuing, before the decay to the 32 decay products of radon at each flash (some products continue to radiate and decay for more seconds) fall down to the floor and immediately combine with dust and anything else there, in atomic sizes. The danger of the 32 now identified decay products of radon has been previously ignored because the decay products were invisible (3700× billion times per second). These invisible products and dust are easily stirred in the air by footsteps of occupants and circulated by home heating air-conditioners to expose occupants living at home. Accordingly, these stirred products (decayed atomic particles and dust, etc) can be circulated even in upper rooms of a home or building where the radioactive decay products can subsequently settle.

Figure 2:
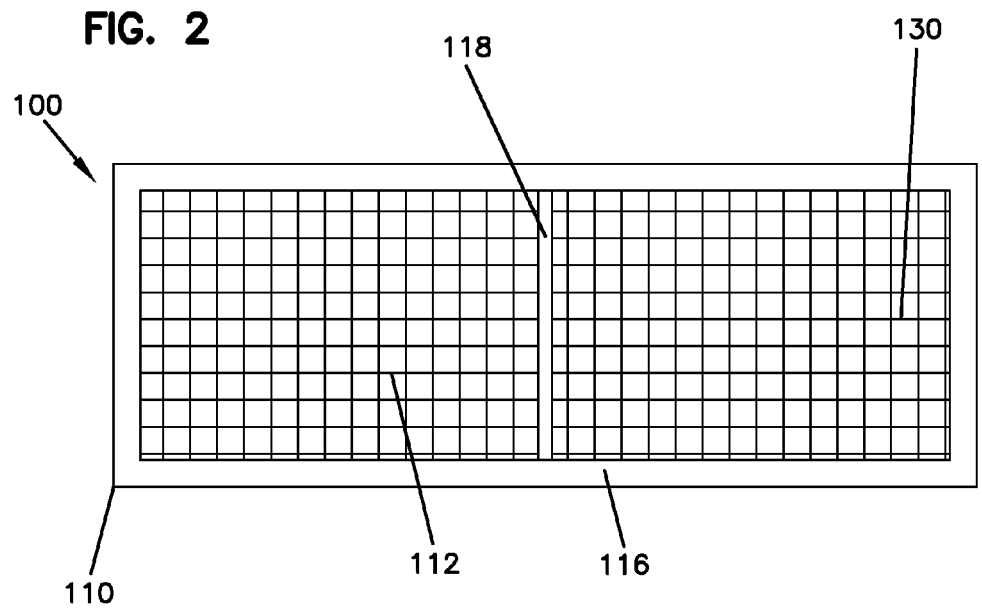
FIG. 2 is a front view of the cartridge shown in FIG. 1.
Figure 3:
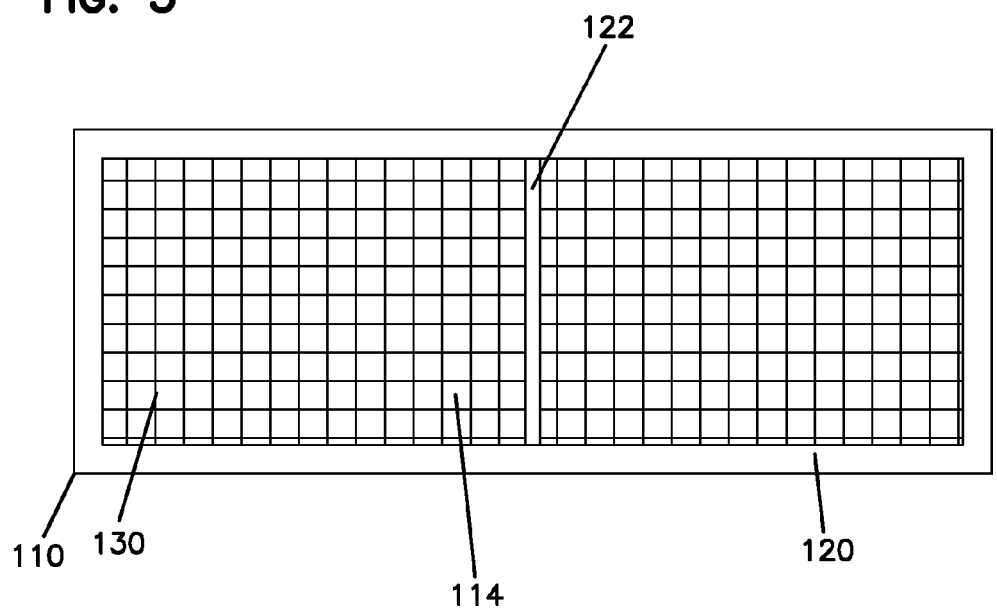
FIG. 3 is a front view of a screen member of the cartridge shown in FIG. 1.

Referring to FIGS. 1-2 a cartridge 100 is shown. The cartridge 100 is for removing radon and/or radon decay products from an air stream passing through the cartridge 100. As shown, the cartridge 100 includes a frame 110 defining a first open face 112 and an opposite second open face 114. The cartridge at the first face 112 is provided with a peripheral flange 116 and a support member 118 that function to retain a screen member 130 (discussed later) within the frame 110. Similarly, the cartridge at the second face 114 is provided with a peripheral flange 120 and a support member 122 that also functions to retain a screen member 130 within the frame 110. It is noted that the frame 110 may be provided with additional or alternative features to flanges 116, 120 and support members 118, 122 to secure one or more screen members 130 within the frame 110.

In one aspect, the frame 110 has a length l1, a width w1, and a height h1. In one embodiment, the length l1 is about 16 inches, the width w1 is about 4 inches, and the height h1 is about six inches. In one embodiment, height h1 is about seven inches. Other dimensions are possible for the frame 110 without departing from the concepts presented herein. In some embodiments, it is desirable that the width w1 be sufficiently large to allow the cartridge to have sufficient stability when placed on a surface, such as a floor surface. Additionally, it is desirable that w1 be greater than the total thickness of the screens 130 such that the screens 130 can be held loosely within the frame rather than being pressed or held tightly against each other. This particular configuration allows for the air flow resistance through the cartridge to remain low as air can travel transversely between the screens 130 to find the next available opening in the screen 130. In some embodiments, it is desirable that height h1 of the cartridge frame 110 be sufficient to allow the highest concentration of radon and radon decay products to pass through the cartridge 100. In some applications, it is believed that the highest concentration of radon and radon decay products can be found at six inches and lower from a floor surface. In one embodiment, the frame 110 is constructed from a paper material, such as cardboard. However, other materials may be used for the frame 110 without departing from the concepts presented herein.

As most easily seen at FIG. 1, the frame 110 houses a plurality of screens 130 through which air must pass when traversing from the first face 112 to the second face 114 of the cartridge 100. By use of the term screen, it is meant to include any body and especially a generally planar body having a plurality of separated or spaced apertures. As shown, the cartridge 100 includes ten screens 130. However, it should be understood that more or fewer screens 130 may be provided within each cartridge 100. For example, only one screen may be provided. More preferably, the cartridge 100 has between 5 and 10 screens, inclusive. By use of the term inclusive, it is meant that the number of screens includes the first and last mentioned number of screens in the identified range (i.e. the cartridge 100 may have 5, 6, 7, 8, 9, or 10 screens).

Figure 4:
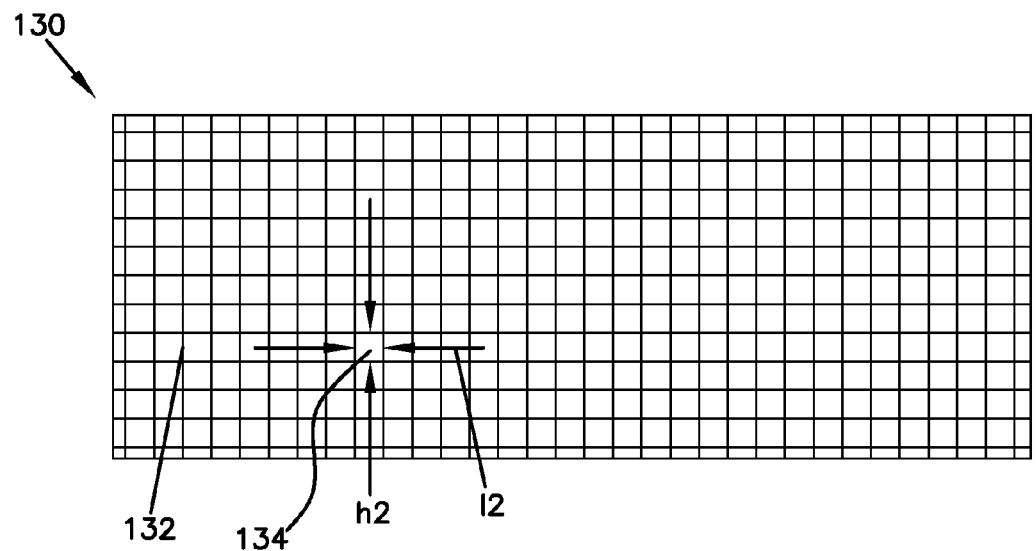
FIG. 4 is a front view of a screen member of the cartridge shown in FIG. 1.

With reference to FIG. 4, each screen 130 has a grid structure 132 defining a plurality of openings 134. As shown, each of the openings 134 has a width w2 and a height h2. In one embodiment, each of the openings 134 has a width w2 of about one half inch and a height h2 of about one half inch. It should be understood that the grid structure 132 could be configured to have different opening sizes and shapes, such as round openings. It is additionally noted that a cartridge 100 could be formed by only one or more screens 130 without the use of a frame 110. In one embodiment, the screens 130 may be manufactured from a plastic material. The screens 130 may also be manufactured from other types of materials, such as a non-plastic material (e.g. paper, cardboard, etc.).

Figure 5:
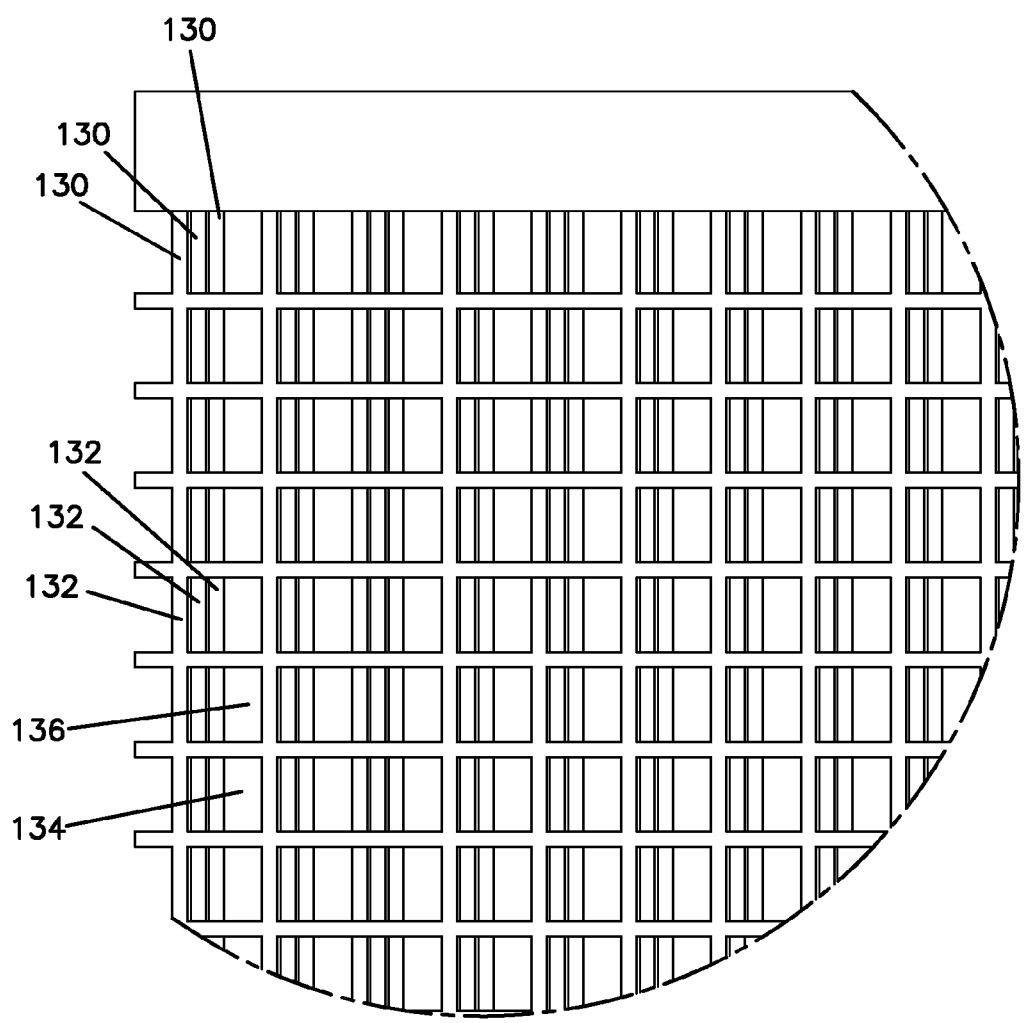
FIG. 5 is a front view of a portion of a plurality of stacked screen members of the cartridge shown in FIG. 1.

With reference to FIG. 5, it can be seen that that the screens can be stacked together such that the openings 134 can be offset or staggered with respect to each other. A staggered arrangement allows for as much of the grid structure 132 of each screen 130 to be exposed to the front and back faces 102, 104 of the cartridge 100. Such an arrangement has the effect of substantially reducing the net opening area 136 defined by the stacked screens which is significantly less than the opening area 134 defined by a single screen. This configuration is desirable because particles passing from the front face 102 to the back face 104 are more likely to come into contact or in close proximity with one or more of the grid structures 132. However, it is noted that it is desirably to allow the screens to be loosely held together rather than tightly so as to allow a low resistance labyrinth-like flow path to be achieved.

In one aspect, the grid structures 132 of one or more of the screens 130 may be provided with a surface that allows the screen(s) 130 to collect and retain radon materials. As used herein, radon materials include radon, any or all of the known decay products of radon, and dust particles to which radon or radon decay products may be attached. Without being held to a particular theory, it is believed that providing a surface or coating (e.g. a negatively charged surface) that stabilizes positive charges in radon materials will operate to attract, collect and retain those materials. In one example, the screens 130 may be provided with a coating that is applied and dried onto the surface of the screen(s) 130. In one embodiment, the coating includes oxides and/or fluorides. In one embodiment, the coating includes inorganic salts and oxides, for example inorganic salts and oxides of magnesium. In one embodiment, the coating includes magnesium fluoride, magnesium oxide, and/or combinations thereof. In one particularly useful embodiment, it is believed that a mixture of fifty percent by weight magnesium fluoride and fifty percent by weight magnesium oxide will yield a high capture rate of radon and radon decay products which may be attached or unattached to dust particles. However, other mixtures of magnesium oxide and magnesium fluoride may be used. For example between about 40 and 60 percent by weight magnesium oxide and between about 40 and 60 percent by weight magnesium fluoride.

Figure 6:
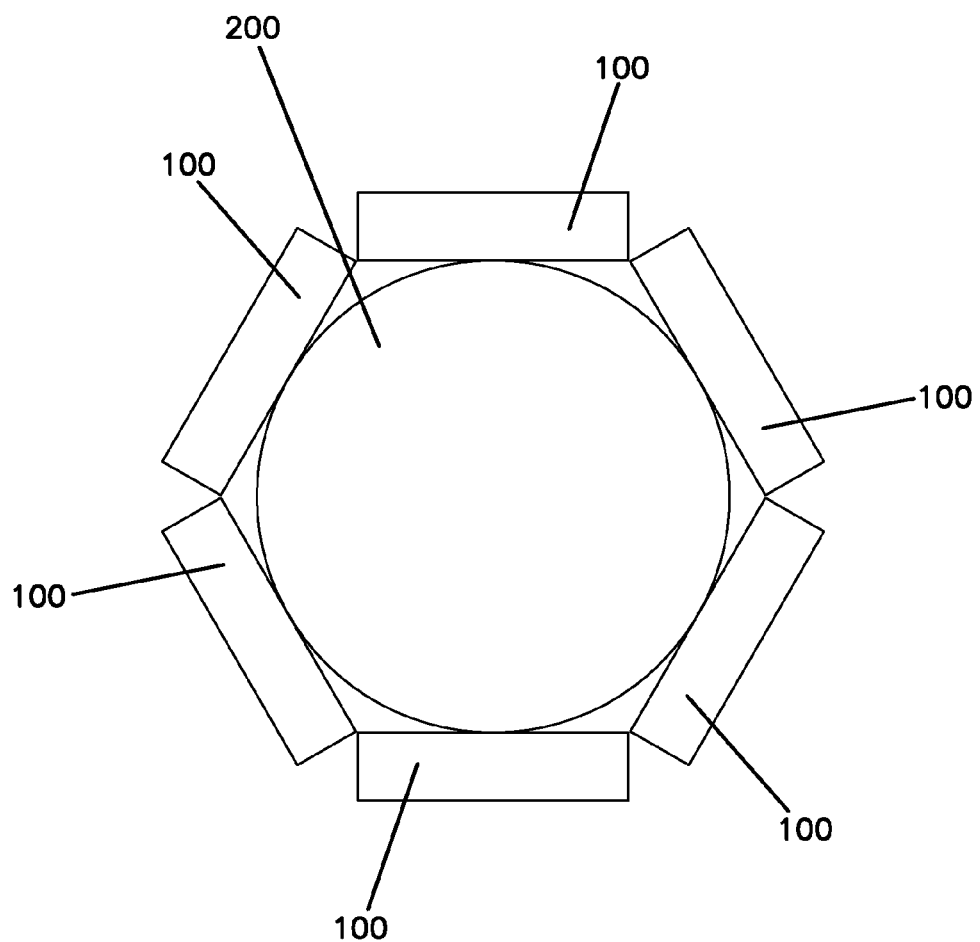
FIG. 6 is a top view of a plurality of the cartridges shown in FIG. 1 arranged about a gas burning appliance.
Figure 7:
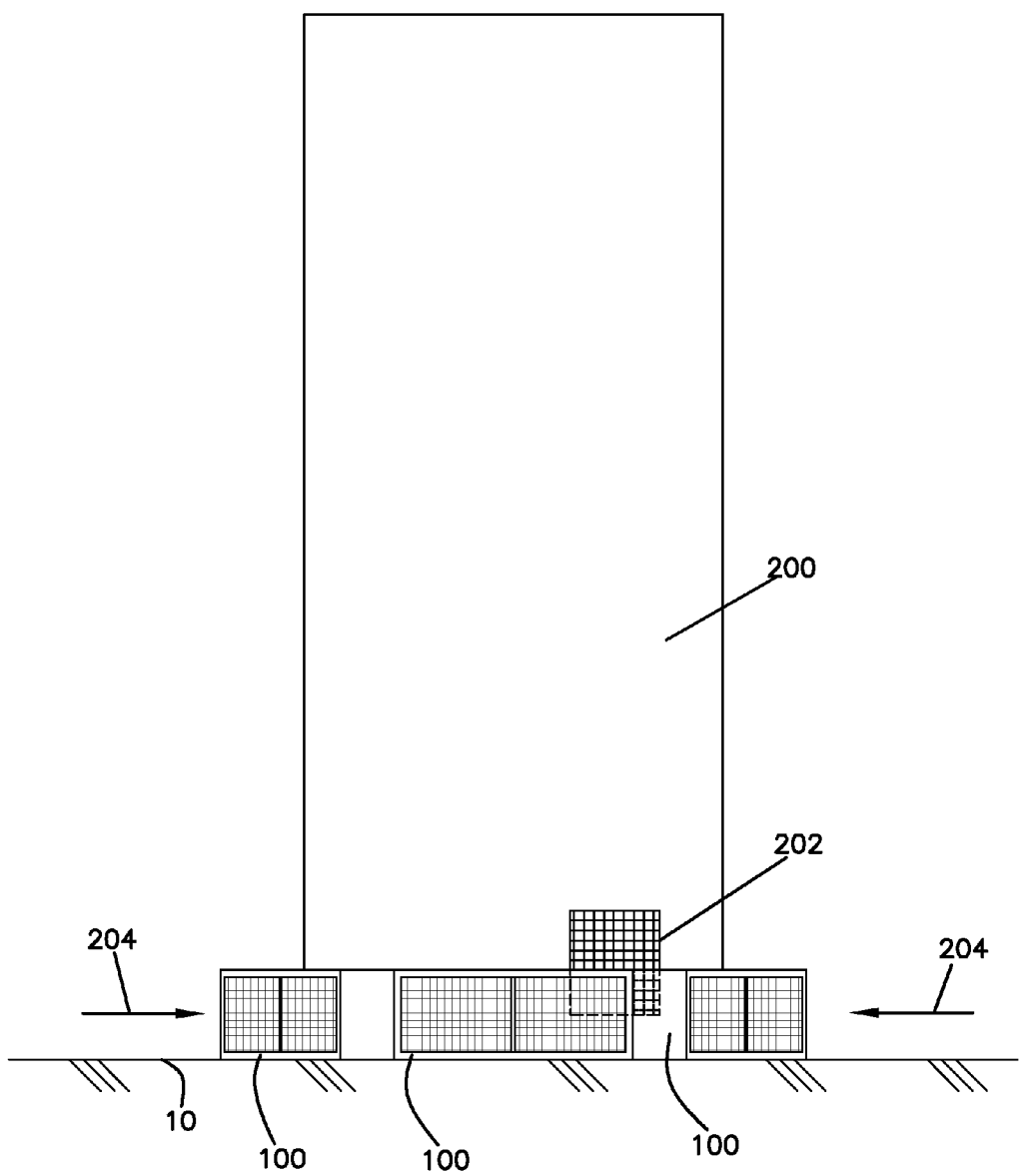
FIG. 7 is a side view of the cartridges and gas burning appliance shown in FIG. 5.

Referring to FIGS. 6-7, one application for the use of cartridges 100 is presented. As shown, a plurality of cartridges 100 are arranged on a floor surface 10 about a gas burning appliance 200. As shown, the gas burning appliance 200 has a combustion air intake 202 which causes an air flow 204 to be induced proximate the floor surface 10. As the induced air travels near the cartridges 100, it is intended that radon and radon decay products, which may be attached or unattached to dust particles, will be captured by the screens 130 within the cartridges 100. Accordingly, the subject matter of the present disclosure represents and distinct advantage over systems which simply exhaust contaminated air from a building structure where the contaminated exhaust may be exposed to people outside of the building structure and/or reintroduced into the building structure. In the embodiment shown, six cartridges 100 are arranged about the gas burning appliance 200. Other numbers and sizes of cartridges 100 may be used without departing from the concepts provided herein. Additionally, the cartridges 100 may be either attached to each other or free-standing and unattached.

Figure 8:
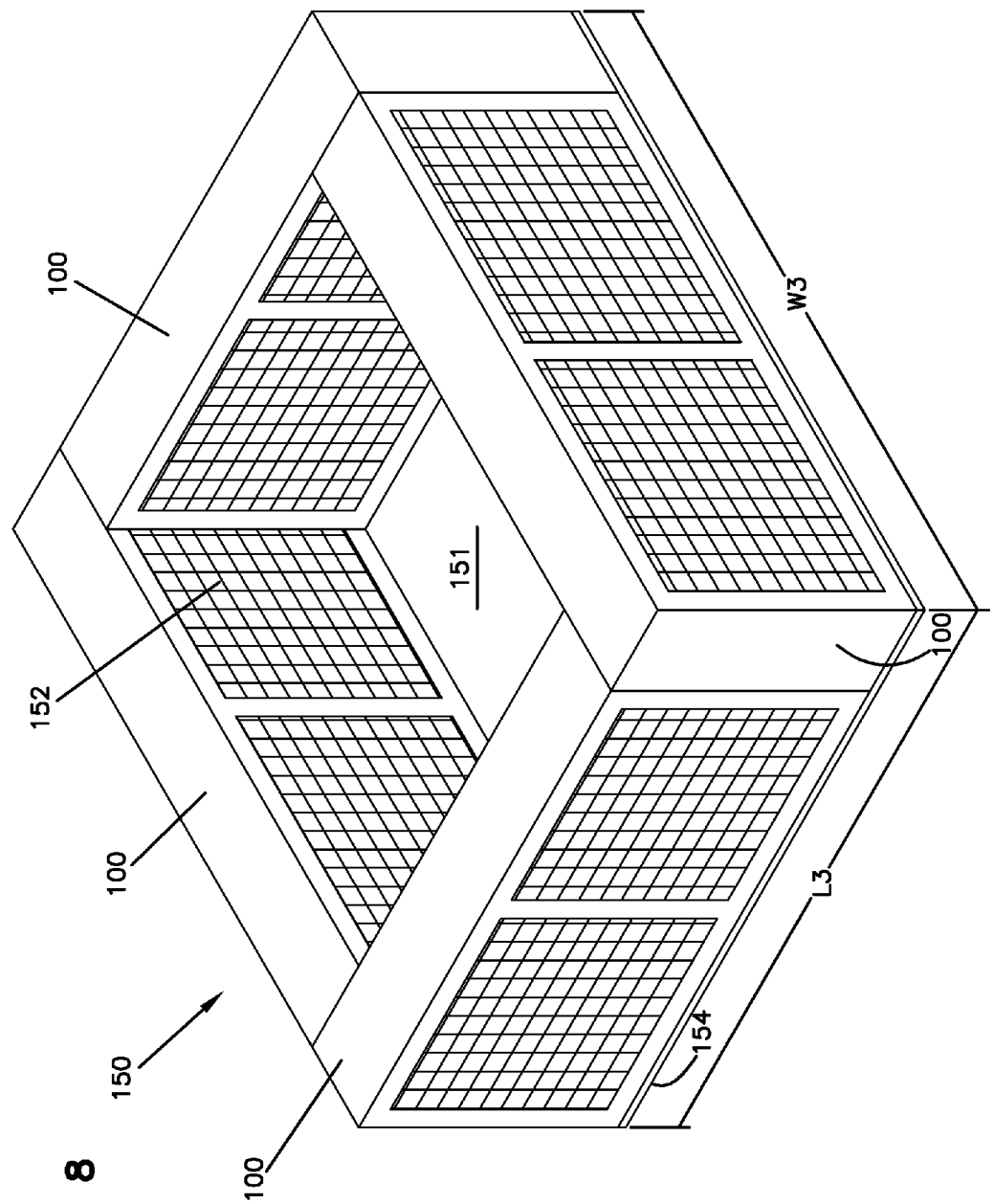
FIG. 8 is a perspective view of a plurality of the cartridges shown in FIG. 1 arranged to form a base structure.

With reference to FIG. 8, four cartridges 100 are arranged to form a base structure 150. As shown, the base structure 150 has a length l3 and a width l4. In one embodiment, length l3 is about 20 inches and width w3 is about 20 inches. Other dimensions and configurations are possible for the base structure 150 by using differently sized and/or arranged cartridges 100. In one embodiment, the cartridges 100 are secured together, for example, by fasteners. It is noted that the base structure could be provided in a circular shape utilizing multiple arc-shaped cartridges 100 or a single cylindrically shaped cartridge 100.

Figure 9:
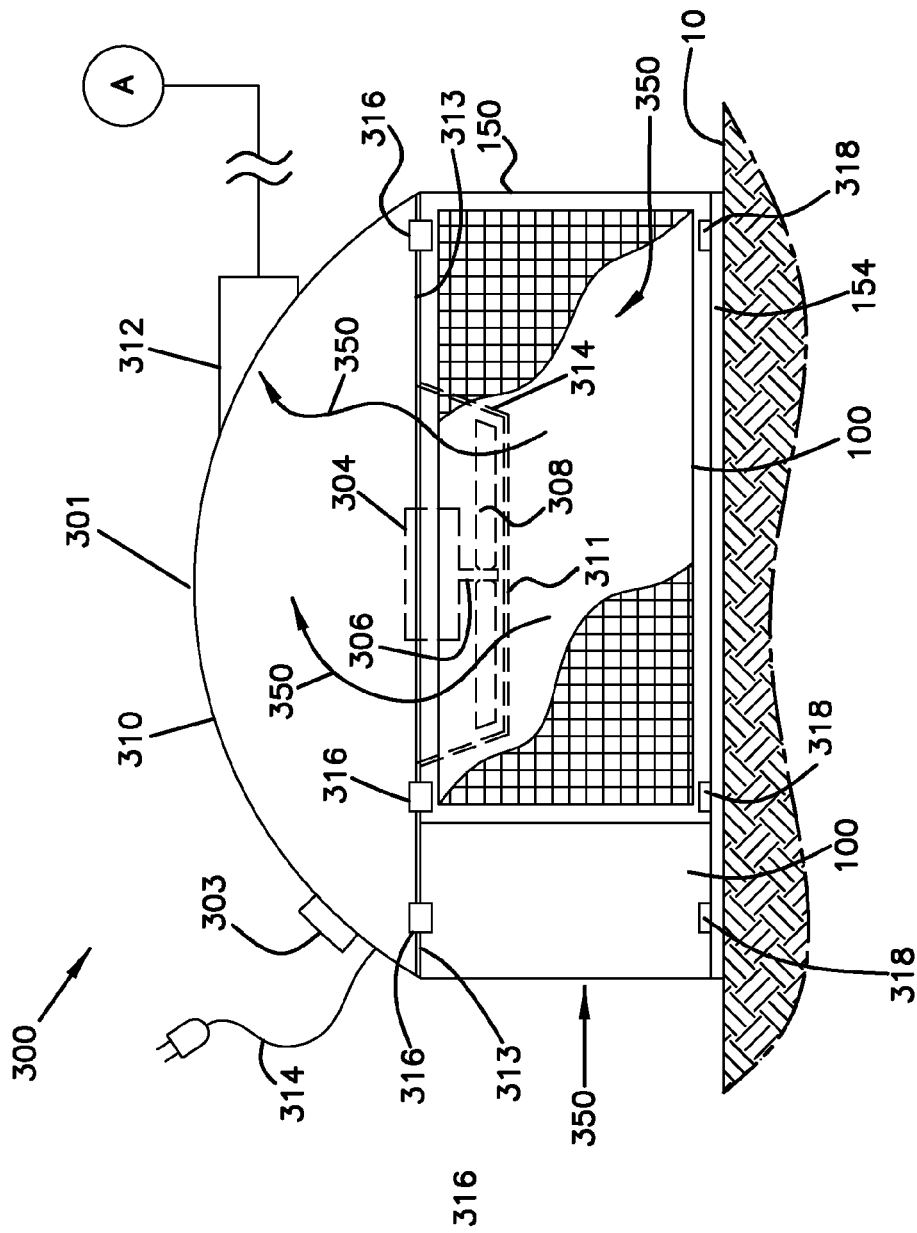
FIG. 9 is a side view of an extraction unit including a fan housing in combination with the base structure shown in FIG. 8.

Referring to FIG. 9, the base structure 150 can be used in conjunction with a fan housing assembly 301 to form an extraction unit 300. In one aspect, the fan housing assembly 301 includes a housing 302 configured to rest upon and be supported by the base structure 150 such that the entire open top portion of the base structure 150 is covered by the housing 302. As shown, the housing 302 includes one or more attachment members 316 via which the cartridges 100 can be attached to the housing 302. In one embodiment, the attachment members 316 are provided as mating clip members on the cartridges 100 and housing 302. It is noted that the housing 302 can alternatively be constructed to extend fully to the floor surface 10 wherein the cartridges 100 are secured within the housing 302 instead of forming a separate base structure 150. Additionally, the housing 302 can also be constructed to hold individual or stacked screens 130 without the need for a formed cartridge 100. In the embodiment shown, the housing 302 has a shape to match the shape provided for the base structure 150. Accordingly, where a square or rectangular base structure 150 is provided, the housing 302 can have a square or rectangular shape at the mounting location. Similarly, a round housing 302 can be provided to interface with a circular-shaped base structure 150.

With continued reference to FIG. 9, the housing 302 further includes an air inlet 311 and an air outlet 312. Adjacent the air inlet is a shroud 314 which extends beyond the bottom side 313 of the housing 302 and past the top of the base structure 150 such that the shroud 314 is at least partially disposed within the central area 151 defined by the base structure 150. The fan housing assembly 301 is also shown as further including a fan motor 304 that is attached to and supported by the housing 302. The fan motor 304 is operatively connected to a drive shaft 306 which is in turn operatively connected to a fan wheel 308 that is disposed in the housing 302 between the inlet 311 and outlet 312. As shown, the motor 304 is connected to a controller 303 and is also provided with a power supply line 314 such that the motor 304 can be powered by an electrical source.

To further support the base structure 150 and to ensure that air is not drawn from between the floor surface 10 and the cartridges 100, a base plate 154 may be provided to cover the bottom opening defined by the central area 151 of the base structure 150. The base plate 154 may be connected directly to the cartridges 100 via attachment members (e.g. mating clips) or may be connected directly to the housing 302.

Figure 10:
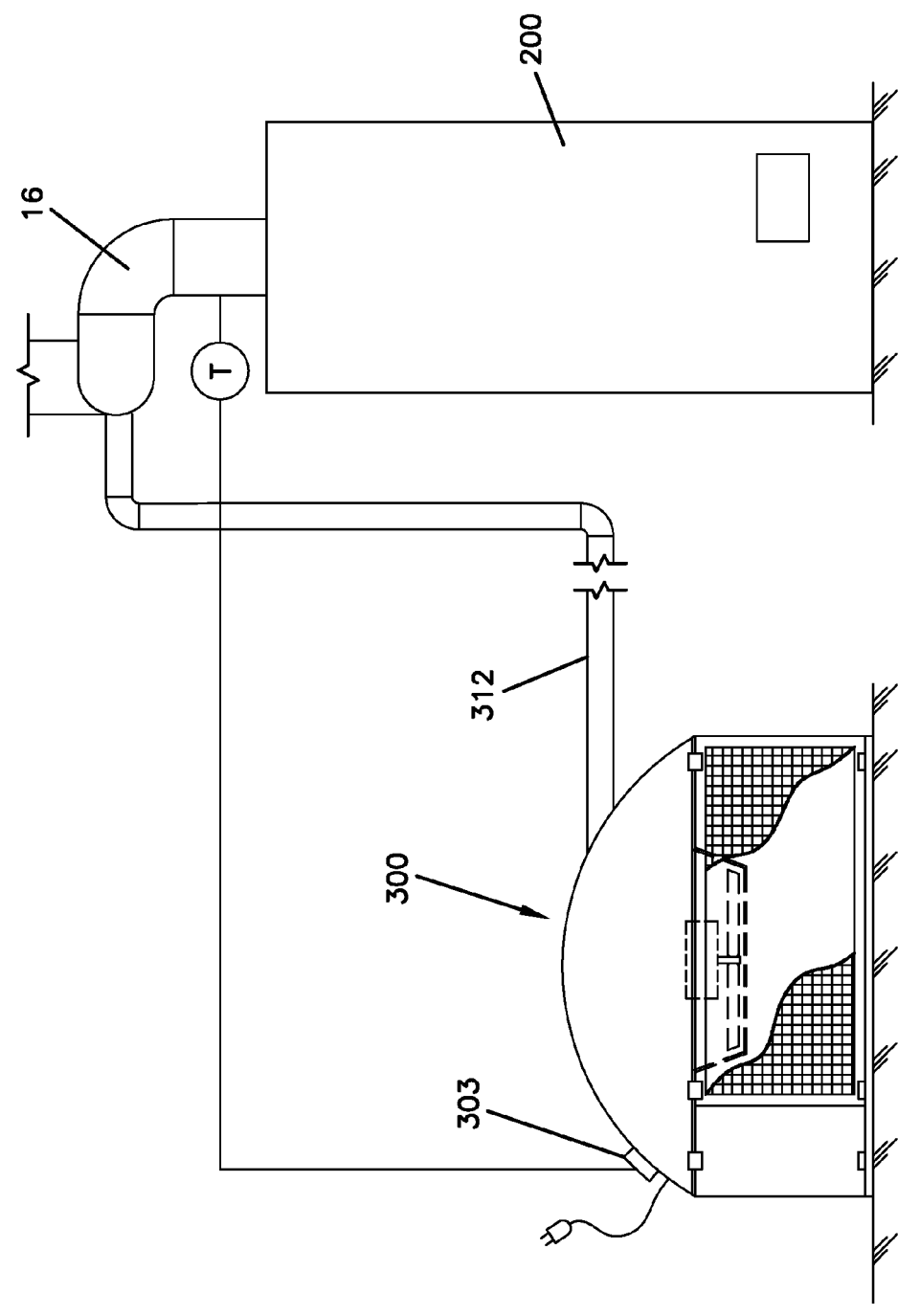
FIG. 10 is a side view of the extraction unit of FIG. 9 that is connected to a gas burning appliance.
Figure 11:
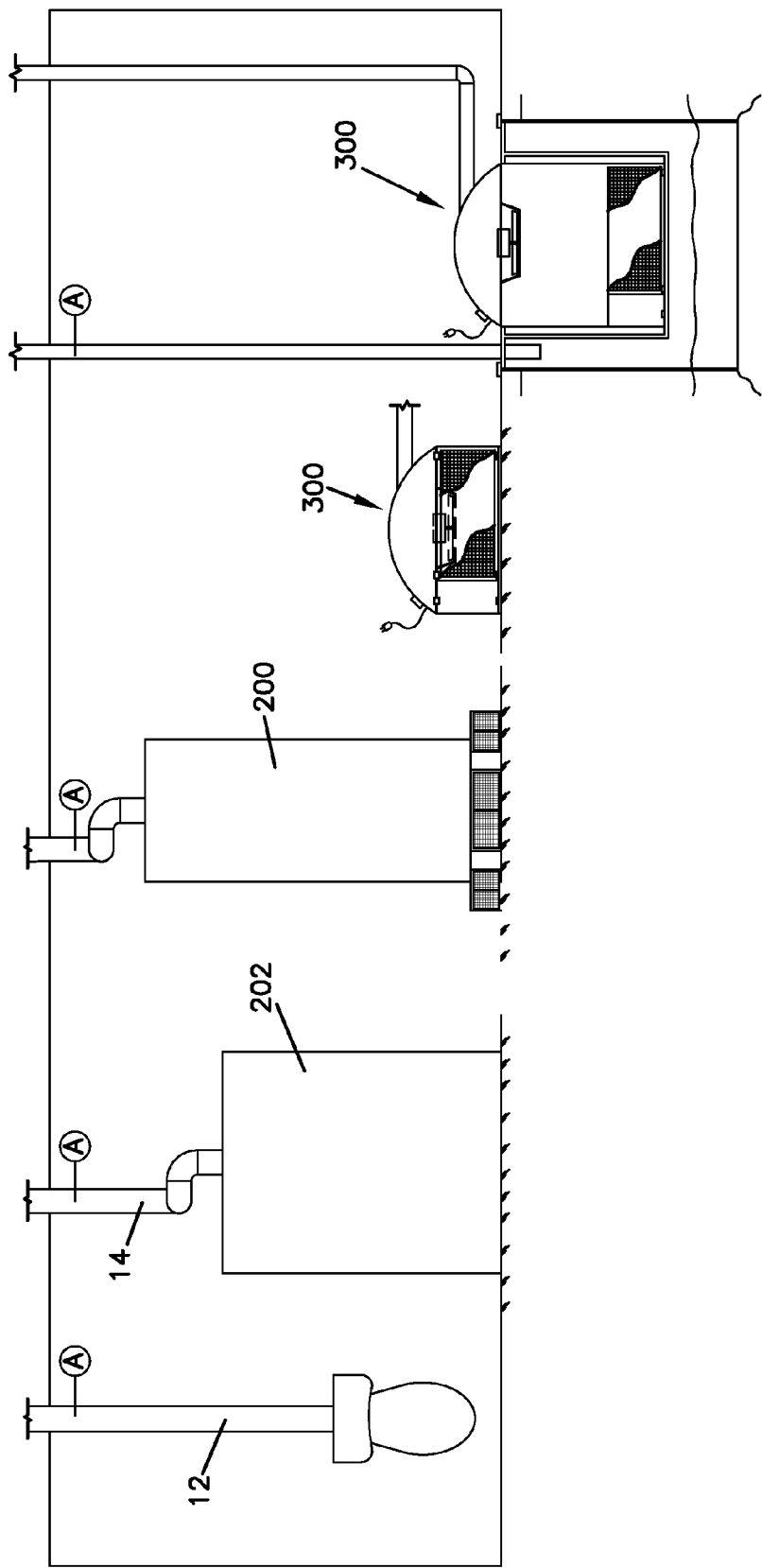
FIG. 11 is a side view of the extraction unit of FIG. 9 showing various connection options.
Figure 13:
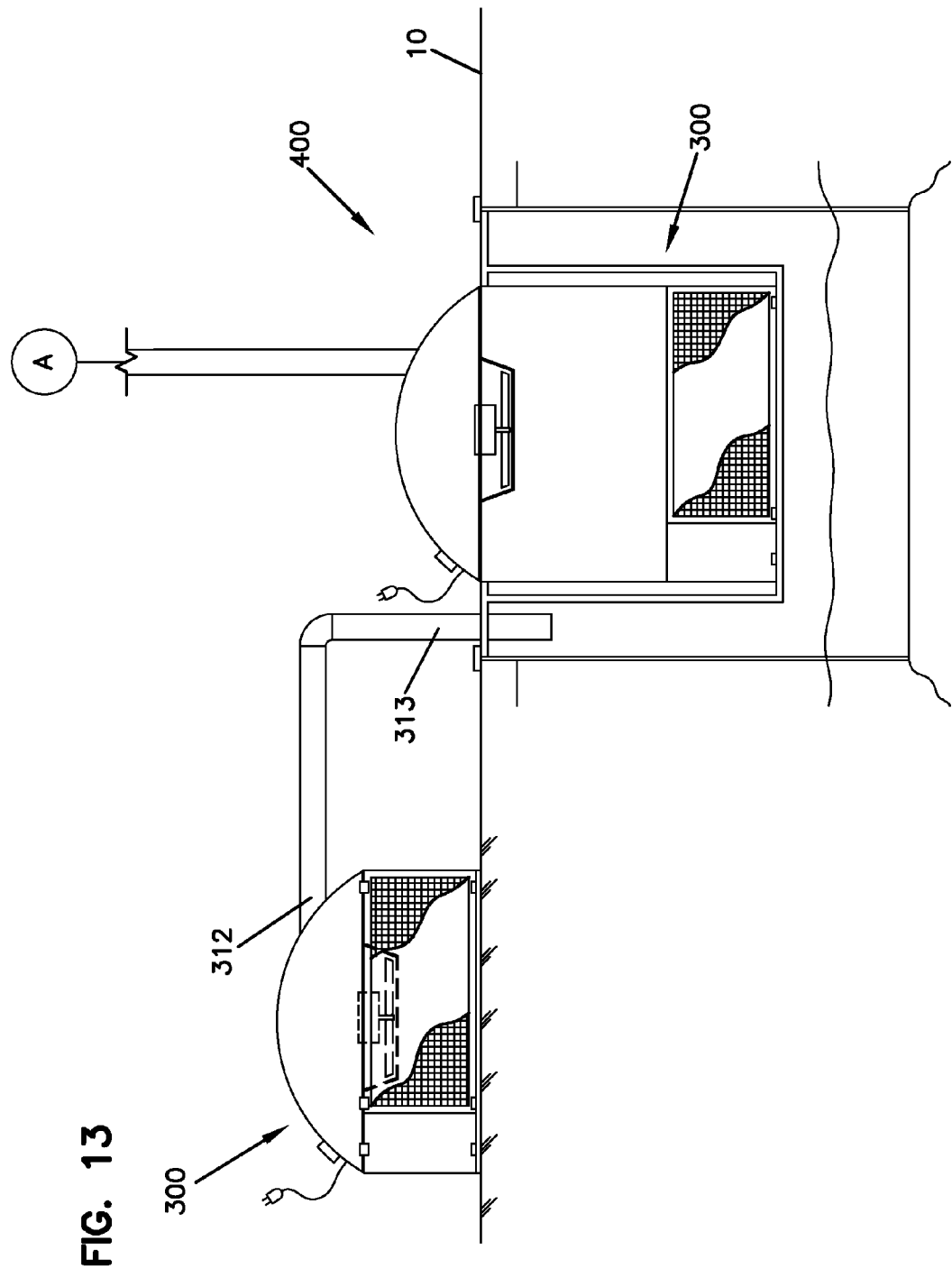
FIG. 13 is a side view of the extraction unit shown in FIG. 9 connected to the in-ground extraction unit shown in FIG. 12.

In operation, the fan wheel 308 is rotated when the motor 304 is energized and an air flow stream 350 is generated in which air flows through the screen(s) 130, into the central area 151, into the shroud 314 via inlet 311, through the fan wheel 308, and out of the outlet 312. As the airflow stream 350 passes through the screen(s) 130, at least some of the radon and/or radon decay products, which may be attached or unattached to dust particles, are captured with any remaining portions being exhausted out of the outlet 312. Outlet 312 may be connected to a conduit or pipe that leads to the outdoors or may be directly routed outdoors. For example, the outlet 312 may be placed in fluid communication with a sanitary waste vent stack 12 extending from one or more plumbing fixtures such as a water closet; a flue 16 of a gas burning appliance 200, such as a water heater; to the flue 14 of another type of gas burning appliance 202; or even into the housing 302 of another extraction unit 300, as shown in the examples of FIGS. 10, 11, and 13. See also location "A" at FIG. 10 for the variously described connection points. As noted previously, it is desirable for the fan wheel 308 to spin slowly enough to induce only a low flow such that the air, radon, radon decay products, and dust at the floor level are not disturbed and can be more easily drawn into the screen(s) 130.

With reference to FIG. 10 specifically, an embodiment is shown in which the motor 304 is activated and deactivated based on the operation of the gas burning appliance 200 such that when the gas burning appliance 200 is deactivated the extraction unit 300 will draw air out of the space. In one embodiment, a temperature sensor placed in the flue of the gas burning appliance 200 is utilized to detect whether the gas burning appliance 200 is operating. In one embodiment, the fan extraction unit 300 has an airflow capacity that generally matches the average combustion air intake flow rate of the gas burning appliance 200. This can be accomplished by selecting an appropriately sized fan wheel 308 and motor 304. Alternatively, the fan motor 304 may be controlled by a variable frequency drive or speed controller such that the desired motor speed can be calibrated during initial set up or installation of the extraction unit 300 to achieve the desired flow rate.

Figure 12:
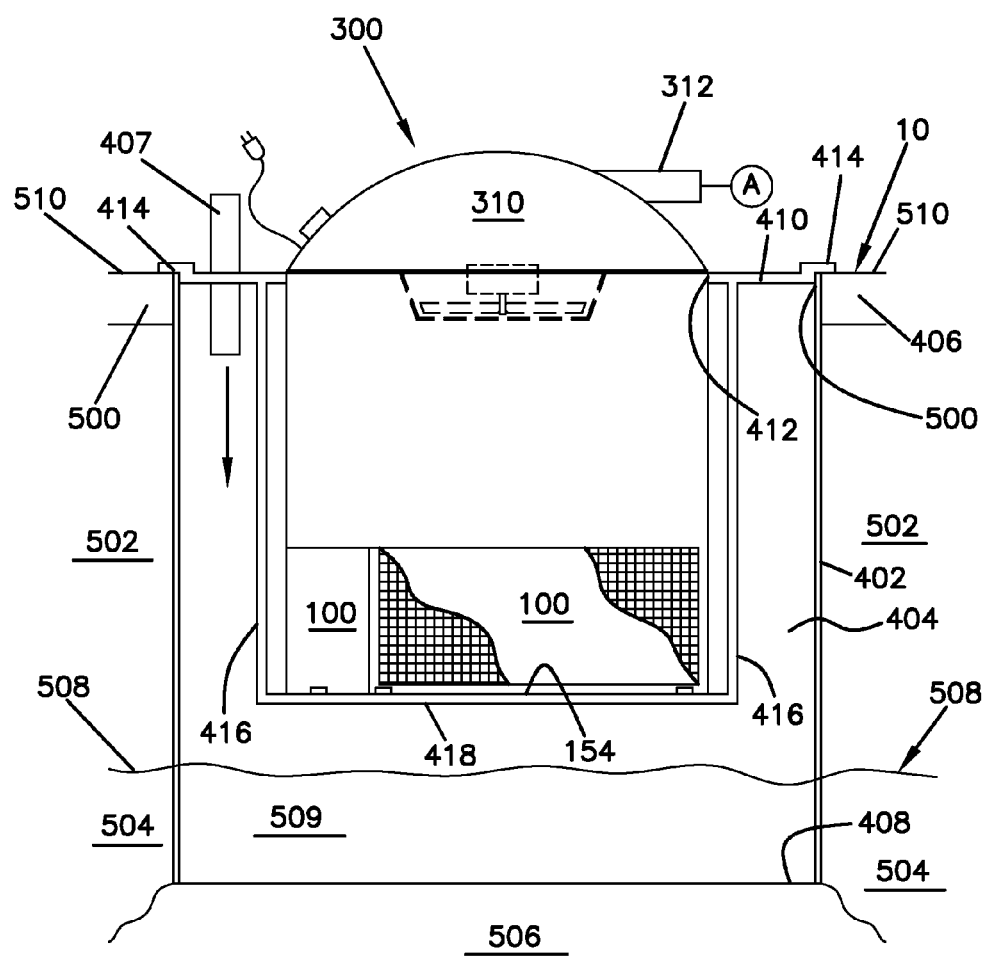
FIG. 12 is a side view of the extraction unit of FIG. 9 installed in an in-ground application.

With reference to FIG. 12, it can be seen that the extraction unit 300 can be configured for use in an underground application. As shown, a sleeve 402 is provided in a floor cavity 501 the ground and has a larger dimension than the housing 302 of the extraction unit 300. In one embodiment, the sleeve 402 is between about 14 inches and about 16" long and has an internal diameter of about 30 inches. In one embodiment, the sleeve 402 has a circular cross-section and is in the form of a cylinder. The sleeve 402 prevents the adjacent earthen materials (e.g. rock, sand, sediment, etc.) from entering the interior space 404 defined by the sleeve 402. In one application, the floor surface 10 is defined by the upper surface 510 of a concrete slab 500. As shown, the concrete slab 500 is supported by a pea gravel or sand layer 502 which is in turn supported by a rock layer 504 which is in turn supported by soil or other earthen materials 506 at the bottom of the floor cavity 501. A rock layer 509 may also be provided within the sleeve 402 as well. In one embodiment, a membrane layer 508 is provided below the rock layer 504 to prevent the migration of radon upwards through the floor slab 500 and to encourage migration into the sleeve 402. It is noted that in some embodiments, it may be advantageous to locate the cylinder near to or in fluid communication with a sanitary vent stack as cavities may be developed around the sanitary sewer lines below the building structure that in turn allow for migration of radon and radon decay products along the sewer lines and towards the sanitary sewer vent stack. This collection dynamic near the plumbing stack may be further exacerbated where coatings have been applied to a floor surface that prevents radon from migrating through the surface.

As shown, the sleeve 402 defines a top opening 406 and a bottom opening 408 and can be provided with any desirable cross-section shape (e.g. rectangular, circular, oval, etc.). At the top opening 406, a cover 410 may be provided that has an opening 412 for the extraction unit 300 and that extends to the opening edges of the floor slab 500. In one embodiment, the cover 410 may be provided with a flange or lip 414 such that the cover 410 can be supported by the floor slab 500. In one embodiment, an inlet tube 407 is provided through the cover 410 such that the exhaust from the outlet 312 of the extraction unit 300 can be connected to the inlet side of the extraction unit shown in FIG. 12. This configuration allows for a single exhaust line to be used where multiple extraction units 300 are utilized, as is the case for the embodiment shown at FIG. 13.

The extraction unit 300 can be supported by a support structure 416 which may extend from the cylinder 402, the cover 410, and/or the floor slab 500. In the particular embodiment shown, the support structure 416 is connected to the cover 410 and extends below the extraction unit 300. In this configuration, the extraction unit 300 can be lowered through the opening 412 and set on the support structure 416. In one embodiment, the support structure 416 includes a bottom plate 418 that simultaneously supports the extraction unit 300 and covers the bottom portion of the extraction unit such that all air removed from the cylinder must pass through the screen (s) 130 before being exhausted. Alternatively, the support structure 416 connects directly to the bottom plate 154 of the extraction unit 300.

Figure 14:
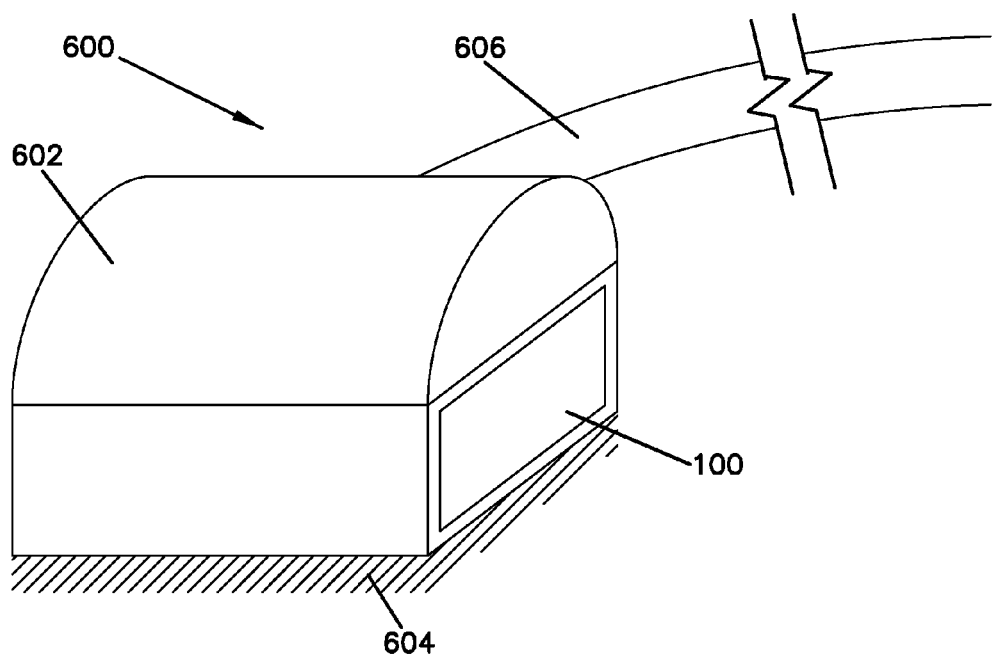
FIG. 14 is a perspective view of a remote vacuum using the cartridge of FIG. 1 that can be connected to the in-ground extraction unit shown in FIG. 12.
Figure 15:
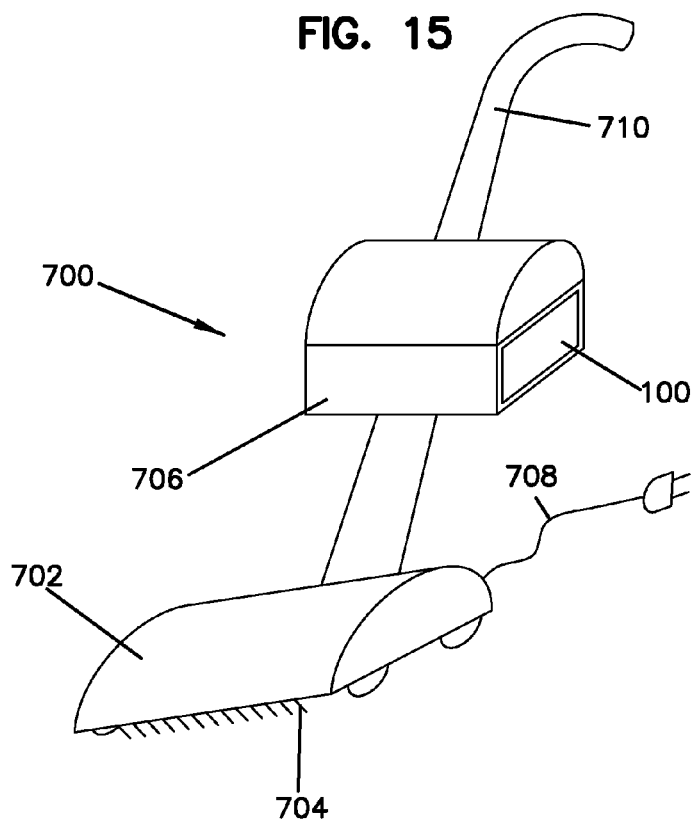
FIG. 15 is a perspective view of a remote powered vacuum using the cartridge of FIG. 1 that can be connected to the in-ground extraction unit shown in FIG. 12.

With reference to FIG. 14, an embodiment is shown where a cartridge 100 is installed within a vacuum head 602 having a scrubber brush 604 and a vacuum hose 606. In one embodiment, the vacuum hose 606 is connected to the inlet tube 407 of the in-ground extraction system shown in FIG. 12. In such a configuration, the extraction unit 300 itself provides the vacuum force at the vacuum head 602 such that a user can actively clean the floor surface 10. Alternatively, a motorized vacuum cleaner 700 having a vacuum source and motorized brushes can be provided in which one or more cartridges 100 can be installed to capture radon and radon decay products which may or may not be attached to dust particles. As shown, the motorized wheeled or non-wheeled vacuum cleaner 700 has a vacuum head 702 with motorized brushes 704, a filter cartridge housing 706, a power cord 708, and a handle 710.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the disclosure.

What is claimed is:

1. A radon material collection cartridge comprising:
    (a) a plurality of radon material collection screens that are stacked proximate each other, each of the plurality of screens having a plurality of spaced openings, at least one of the plurality of screens being provided with a surface that collects and retains radon materials; and
    (b) a frame holding the plurality of screens;
    (c) wherein the surface that collects and retains radon materials is provided as a coating on the at least one radon material collection screen, and wherein the coating comprises at least one of magnesium fluoride and magnesium oxide.

2. The radon collection cartridge of claim 1, wherein the plurality of radon material collection screens are offset with respect to each other such that at least some of the spaced openings of the plurality of radon material collection screens are offset with respect to each other.

3. The radon material collection cartridge of claim 2, wherein the plurality of radon material collection screens includes five to ten stacked screens, inclusive.

4. The radon collection cartridge of claim 1, wherein the frame has a first width that is greater than a sum of individual thicknesses of the radon material collection screens.

5. The radon collection cartridge of claim 1, wherein the coating comprises a mixture of magnesium fluoride and magnesium oxide.

6. The radon collection cartridge of claim 5, wherein the mixture of magnesium fluoride and magnesium oxide is between 40 and 60 percent, by weight, magnesium fluoride with the remaining portion being magnesium oxide.

7. A radon extraction system comprising:
(a) at least one radon material collection device including at least one screen having a plurality of spaced openings and having a surface that collects and retains radon materials;
(b) a fan assembly having a motor connected to a fan wheel constructed and arranged to induce an air flow through the at least one radon material collection screen when the motor is activated; and
(c) a controller that selectively activates and deactivates the fan assembly motor;
(d) wherein the at least one screen includes a plurality of stacked radon material collection screens retained in a frame to form a radon material collection cartridge, and wherein a base frame structure is formed from four radon material collection cartridges arranged in a rectangular configuration to form a central opening.

8. The radon extraction system of claim 7, wherein the controller is configured to activate and deactivate the fan assembly motor based on the operational state of a gas burning appliance.

9. The radon extraction system of claim 8, wherein:
(a) the gas burning appliance is a water heater;
(b) a temperature sensor is located in an exhaust flue of the water heater and in communication with the controller; and
(c) the controller activates and deactivates the fan assembly motor based on a temperature sensed at the temperature sensor.

10. The radon extraction system of claim 7, further comprising:
(a) a sleeve within which the at least one radon collection device is disposed.

11. The radon collection cartridge of claim 7, wherein the surface that attracts radon materials is provided as a coating on the at least one screen.

12. The radon collection cartridge of claim 11, wherein the coating comprises at least one of magnesium fluoride and magnesium oxide.

13. The radon collection cartridge of claim 12, wherein the coating comprises a mixture of magnesium fluoride and magnesium oxide.

\* \* \* \* \*